(12) United States Patent
Chiang et al.

(10) Patent No.: US 8,648,215 B2
(45) Date of Patent: Feb. 11, 2014

(54) SPIROENONE AND USES THEREOF

(75) Inventors: Wenchang Chiang, Kaohsiung (TW);
Yueh-Hsiung Kuo, Kaohsiung (TW);
Yun-Lian Lin, Kaohsiung (TW);
Cheng-Pei Chung, Kaohsiung (TW)

(73) Assignee: Joben Bio-Medical Co., Ltd., Pingtung County (TW)

( * ) Notice: Subject to any disclaimer, the term of this patent is extended or adjusted under 35 U.S.C. 154(b) by 26 days.

(21) Appl. No.: 13/364,127

(22) Filed: Feb. 1, 2012

(65) Prior Publication Data
US 2013/0197097 A1 Aug. 1, 2013

(51) Int. Cl.
*C07C 45/79* (2006.01)
*C07C 49/753* (2006.01)
*A61K 31/122* (2006.01)

(52) U.S. Cl.
USPC ............ 568/338; 568/366; 568/377; 514/691

(58) Field of Classification Search
USPC ........................... 568/338, 366, 377; 514/691
See application file for complete search history.

(56) References Cited

PUBLICATIONS

Huang, S. L.; Chen, Y. F.; Chiang, W., Amino acids, fatty acids, and proximate composition of the seed of adlay, Food Sci. 1994, 21, 67-74.

Lee, M. Y.; Tsai, S. H.; Kuo, Y. H.; Chiang, W., Anti-tumor and anti-inflammatory activity of the methanol extracts from adlay bran, Food Sci. Biotechnol. 2008, 17, 1265-1271.

Lee, M. Y.; Lin, H. Y.; Cheng, F.; Chiang, W. C.; Kuo, Y. H. Isolation and characterization of new lactam compounds that inhibit lung and colon cancer cells from adlay (*Coix lachiyma-jobi* L. var. mayuen Stapf) bran. Food Chem. Toxicol. 2008, 46, 1933-1999.

Chen, H. J.; Shih, C. K.; Hsu, H. Y.; Chiang, W. Mast cell-dependent allergic responses are inhibited by ethanolic extract of adlay (*Coix lachryma-jobi* L. var. ma-yuen Stapf.) testa. J. Agric. Food Chem. 2010, 58, 2596-2601.

Tanimura, A. Studies on the anti-tumor component in the seeds of *Coix lachryma-jobi* L. var. ma-yuen (Roman.) Stapf. II. The structure of coixenolide. Chem. Pharm. Bull. 1961, 9, 47-53.

Tokuda, H.; Matsumoto, T.; Konoshima, T.; Kozuka, M.; Nishino, H.; Iwashima, A. Inhibitory effects on Epstein-Barr virus activation and anti-tumor promoting activities of Coix seed. Planta Med. 1990, 56, 653-654.

Woo, J. H.; Li, D.; Wilsbach, K.; Orita, H.; Coulter, J.; Tully, E.; Kwin, T. K.; Xu, S.; Gabrielson, E. Coix seed extract, a commonly used treatment for cancer in China, inhibits NFκb and protein kinase C signaling. Cancer Biol. Ther. 2007, 6, 2005-2010.

Yu, F.; Gao, J.; Zeng, Y.; Liu, C. X. Inhibition of Coix seed extract on fatty acid synthase, a novel target for anticancer activity. J. Ethnopharmacol. 2008, 119, 252-258.

Lu, Y.; Wu, L. Q.; Dong, Q.; Li, C. S. Experimental study on the effect of Kang-Lai-Te induced apoptosis of human heptoma carcinoma cell HepG2. Hepatobiliary Pancreatic Dis. Int. 2009, 8, 267-272.

Chung, C. P.; Hsu, H. Y.; Huang, D. W.; Hsu, H. H.; Lin, J. T.; Shih, C. K.; Chiang, W. Ethyl acetate fraction of adlay bran ethanolic extract inhibits oncogene expression and suppresses DMH-induced preneoplastic lesions of the colon in F344 rats through an anti-inflammatory pathway. J. Agric. Food Chem. 2010, 58, 7616-7623.

Hsia, S. M.; Yeh, C.; Kuo, Y. H.; Wang, P. S.; Chiang, W. Effects of adlay (*Coix lachryma-jobi* L. var. ma-yuen Stapf.) hull extracts on the secretion of progesterone and estradiol in vivo and in vitro. Exp. Biol. Med. 2007, 232, 1181-1194.

Hsia, S. M.; Tseng, Y. W.; Wang, S. W.; Kuo, Y. H.; Huang, D. W.; Wang, P. S.; Chiang, W. Effect of adlay (*Coix lachryma-jobi* L. var. ma-yuen Stapf.) hull extracts on testosterone release from rat Leydig cells. Phytother. Res. 2009, 23, 687-695.

Ho, C. Y.; Kim, C, F.; Leung, K. N.; Fung, K. P.; Tse, T. F.; Chan, H.; Lau, C. B. Differential anti-tumor activity of *Coriolus versicolor* (Yunzhi) extract through p53- and/or Bcl-2-dependent apoptotic pathway in human breast cancer cells. Cancer Biol. Ther. 2005, 4, e11-e17.

Meegan, M. J.; Carr, M.; Knox, A. J. S.; Zisterer, D. M.; loyd, D. G. β-Lactam type molecular scaffolds for antiproliferative activity: Synthesis and cytotoxic effects in breast cancer cells. J. Enzyme Inhib. Med. Chem. 2008, 23, 668-685.

Davis, R. A.; Carroll, A. R.; Andrews, K. T.; Boyle, G. M.; Tran, T. L.; Healy, P. C.; Kalaitzis, J. A.; Shivas, R. G. Pestalactams A-C: Novel caprolactams from the endophytic fungus *Pestalotiopsis* sp. Org. Biomol. Chem. 2010, 8, 1785-1790.

Kwon, H. K.; Ahn, S. H.; Park, S. H.; Park, J. H.; Park, J. W.; Kim, H. M.; Park, S. K.; Lee, K.; Lee, C. W.; Choi, E.; Han, G.; Han, J. W. A novel γ-lactam-based histone deacetylase inhibitor potently inhibits the growth of human breast and renal cancer cells. Biol. Pharm. Bull. 2009, 32, 1723-1727.

Cheng-Pei Chung, Chih-Ying Hsu, Jing-Hui Lin, Yueh-Hsiung Kuo, Wenchang Chiang, and Yun-Lian Lin. Antiproliferative Lactams and Spiroenone from Adlay Bran in Human Breast Cancer Cell Lines. J. Agric. Food Chem. 2011, 59, 1185-1194.

*Primary Examiner* — Sikarl Witherspoon
(74) *Attorney, Agent, or Firm* — WPAT, P.C.; Anthony King (57) ABSTRACT

The present invention provides novel spiroenones extracted from an alcohol extract of dehulled adlay seeds. The present invention also provides a process for the preparation of the spiroenones and a method for treating breast cancer in a subject, which method comprises administering to said subject an effective amount of the spiroenone and a pharmaceutically acceptable carrier or excipient.

24 Claims, 5 Drawing Sheets

SPIROENONE AND USES THEREOF

BACKGROUND OF THE INVENTION

1. Field of the Invention

The invention relates to novel spiroenones extracted from an alcohol extract of dehulled adlay seeds and uses thereof.

2. Description of the Related Art

Adlay (*Coix lachryma-jobi* L. var. *ma-yuen* Stapf) is a grass crop and mainly planted in India, Taiwan, Japan, and China (Huang, S. L.; Chen, Y. F.; Chiang, W. Amino acids, fatty acids, and proximate composition of the seed of adlay. *Food Sci.* 1994, 21, 67-74). The seeds of adlay are also known as Chinese pearl barley and soft-shelled Job's tears. Adlay seeds have long been used in traditional Chinese medicine (TCM) to treat inflammation, dysfunctions of the endocrine system, warts, chapped skin, rheumatism, and neuralgia and also as a nourishing food (Li, S. C. *Pen-t'sao kang mu (Systematic Pharmacopoeia)*; China, 1596). Dehulled adlay (DA) is believed to be beneficial to humans, and many processed products from adlay are manufactured as healthy foods or food supplements (Huang, S. L.; Chen, Y. F.; Chiang, W. Amino acids, fatty acids, and proximate composition of the seed of adlay. *Food Sci.* 1994, 21, 67-74). The DA is composed of about 8% bran and 92% endosperm, and previous studies showed that the adlay bran (AB) possesses anti-inflammatory, antiproliferative, and antiallergic activities better than the endosperm (Lee, M. Y.; Tsai, S. H.; Kuo, Y. H.; Chiang, W. Anti-tumor and anti-inflammatory activity of the methanol extracts from adlay bran. *Food Sci. Biotechnol.* 2008, 17, 1265-1271; Lee, M. Y.; Lin, H. Y.; Cheng, F.; Chiang, W. C.; Kuo, Y. H. Isolation and characterization of new lactam compounds that inhibit lung and colon cancer cells from adlay (*Coix lachryma-jobi* L. var. *mayuen* Stapf) bran. *Food Chem. Toxicol.* 2008, 46, 1933-1999; Chen, H. J.; Shih, C. K.; Hsu, H. Y.; Chiang, W. Mast celldependent allergic responses are inhibited by ethanolic extract of adlay (*Coix lachryma-jobi* L. var. *ma-yuen* Stapf.) testa. *J. Agric. Food Chem.* 2010, 58, 2596-2601).

In line with the medicinal uses of adlay, many studies have been performed to evaluate its effects. A series of studies on antitumorrelated activities of adlay seeds have been reported. Coixenolide (Tanimura, A. Studies on the anti-tumor component in the seeds of *Coix lachryma-jobi* L. var. *ma-yuen* (Roman.) Stapf. II. The structure of coixenolide. *Chem. Pharm. Bull.* 1961, 9, 47-53), fatty acids (Tokuda, H.; Matsumoto, T.; Konoshima, T.; Kozuka, M.; Nishino, H.; Iwashima, A. Inhibitory effects on Epstein-Barr virus activation and anti-tumor promoting activities of *Coix* seed. *Planta Med.* 1990, 56, 653-654), and a neutral lipid extract (Woo, J. H.; Li, D.; Wilsbach, K.; Orita, H.; Coulter, J.; Tully, E.; Kwin, T. K.; Xu, S.; Gabrielson, E. *Coix* seed extract, a commonly used treatment for cancer in China, inhibits NFκB and protein kinase C signaling. *Cancer Biol. Ther.* 2007, 6, 2005-2010; Yu, F.; Gao, J.; Zeng, Y.; Liu, C. X. Inhibition of *Coix* seed extract on fatty acid synthase, a novel target for anticancer activity. *J. Ethnopharmacol.* 2008, 119, 252-258; Lu, Y.; Wu, L. Q.; Dong, Q.; Li, C. S. Experimental study on the effect of Kang-Lai-Te induced apoptosis of human hepatoma carcinoma cell HepG2. *Hepatobiliary Pancreatic Dis. Int.* 2009, 8, 267-272) have been claimed as its active components. Lee et al. reported that a methanolic extract of AB had antitumor and anti-inflammatory activities (Lee, M. Y.; Tsai, S. H.; Kuo, Y. H.; Chiang, W. Anti-tumor and anti-inflammatory activity of the methanol extracts from adlay bran. *Food Sci. Biotechnol.* 2008, 17, 1265-1271) and that cytotoxic lactams have been isolated (Lee, M. Y.; Lin, H. Y.; Cheng, F.; Chiang, W. C.; Kuo, Y. H. Isolation and characterization of new lactam compounds that inhibit lung and colon cancer cells from adlay (*Coix lachryma-jobi* L. var. *mayuen* Stapf) bran. *Food Chem. Toxicol.* 2008, 46, 1933-1999). Additionally, the ethyl acetate (EA) fraction of AB ethanolic extract (ABE-EA) is shown to suppress aberrant crypt foci (ACF) in dimethyl hydrazine (DMH)-induced colon carcinogenesis (Chung, C. P.; Hsu, H. Y.; Huang, D. W.; Hsu, H. H.; Lin, J. T.; Shih, C. K.; Chiang, W. Ethyl acetate fraction of adlay bran ethanolic extract inhibits oncogene expression and suppresses DMH-induced preneoplastic lesions of the colon in F344 rats through an anti-inflammatory pathway. *J. Agric. Food Chem.* 2010, 58, 7616-7623).

The modulatory effects in the endocrine system of adlay seeds have been reported (Hsia, S. M.; Yeh, C.; Kuo, Y. H.; Wang, P. S.; Chiang, W. Effects of adlay (*Coix lachryma-jobi* L. var. *ma-yuen* Stapf.) hull extracts on the secretion of progesterone and estradiol in vivo and in vitro. *Exp. Biol. Med.* 2007, 232, 1181-1194; Hsia, S. M.; Tseng, Y. W.; Wang, S. W.; Kuo, Y. H.; Huang, D. W.; Wang, P. S.; Chiang, W. Effect of adlay (*Coix lachryma-jobi* L. var. *ma-yuen* Stapf.) hull extracts on testosterone release from rat Leydig cells. *Phytother. Res.* 2009, 23, 687-695). Human breast cancer cells that express estrogen receptor (ER) and prostate cancer cells that express androgen receptor (AR) are closely involved with cells that secrete hormone; they are regarded as benign but possibly may turn into a malignant tumor (Ho, C. Y.; Kim, C, F.; Leung, K. N.; Fung, K. P.; Tse, T. F.; Chan, H.; Lau, C. B. Differential anti-tumor activity of *Coriolus versicolor* (Yunzhi) extract through p53- and/or Bcl-2-dependent apoptotic pathway in human breast cancer cells. *Cancer Biol. Ther.* 2005, 4, e11-e17). Nonetheless, the effects of AB on endocrine related cancer cells and related components of adlay bran remain unclear.

SUMMARY OF THE INVENTION

In the present invention, novel spiroenones extracted from an alcohol extract of dehulled adlay seeds are provided. Moreover, the antiproliferative activities against the breast cancer cell line of the spiroenones are elucidated.

The invention provides a spiroenone of formula (I):

or a pharmaceutically acceptable derivative thereof,
wherein $R_1$ to $R_4$ is dependently H or an alkyl group having 1 to 6 carbon atoms.

The invention also provides a composition comprising the spiroenone as mentioned above and optionally a pharmaceutically acceptable carrier or excipient.

The invention further provides a process for the preparation of the spiroenone as mentioned above, which process comprises the steps of:
(a) providing adlay bran from dehulled adlay seeds;
(b) extracting the adlay bran in step (a) with an alcohol solution to obtain an alcohol extract;

(c) sequential partitioning the ethanol extract in step (b) with hexane and ethyl acetate to obtain an ethyl acetate fraction;

(d) subfractioning the ethyl acetate fraction in step (c) with column chromatography with successive elution by an ethyl acetate/hexane gradient ant methanol solvent to obtain an ethyl acetate/hexane subfration; and (e) isolating the spiroenone from the subfraction in step (d) by high-performance liquid chromatography.

The invention also provides a method for treating breast cancer in a subject, which comprises administering to said subject an effective amount of the spiroenone as mentioned above and a pharmaceutically acceptable carrier or excipient.

DETAILED DESCRIPTION OF THE INVENTION

The present invention can be more readily understood by reference to the following detailed description of various embodiments of the invention, the examples, and the chemical drawings and tables with their relevant descriptions. It is to be understood that unless otherwise specifically indicated by the claims, the invention is not limited to specific preparation methods, carriers or formulations, or to particular modes of formulating the compounds of the invention into products or compositions intended for topical, oral or parenteral administration, because as one of ordinary skill in the relevant arts is well aware, such things can, of course, vary. It is also to be understood that the terminology used herein is for the purpose of describing particular embodiments only and is not intended to be limiting.

As utilized in accordance with the present disclosure, the following terms, unless otherwise indicated, shall be understood to have the following meaning:

As used herein, the term "alkyl" includes straight and branched chains.

"Alkyl" refers to a hydrocarbon group that can be conceptually formed from an alkane by removing hydrogen from the structure of a non-cyclic hydrocarbon compound having straight or branched carbon chains, and replacing the hydrogen atom with another atom or organic or inorganic substituent group. In some embodiments of the invention, the "alkyl group having 1 to 6 carbon atoms" such as methyl, ethyl, propyl, isopropyl, n-butyl, iso-butyl, sec-butyl, tert-butyl, amyl, tert-amyl, hexyl and the like.

The term "a pharmaceutically acceptable derivative" or "pharmaceutically acceptable derivatives" as used herein denotes a compound that is modified from the compound of the invention but that has properties and efficacies that are the same as or better than those of the compound of the invention. Preferably, the pharmaceutically acceptable derivative is a pharmaceutically acceptable salt, solvate, hydrate, or prodrug of the compound of the invention.

One or more of the compounds of the invention may be present as a salt. The term "salt" encompasses those salts formed with the organic and inorganic anions and cations. Furthermore, the term includes salts that form by standard acid-base reactions with basic groups and organic or inorganic acids. Such acids include hydrochloric, hydrofluoric, trifluoroacetic, sulfuric, phosphoric, acetic, succinic, citric, lactic, maleic, fumaric, palmitic, cholic, pamoic, mucic, D-glutamic, D-camphoric, glutaric, phthalic, tartaric, lauric, stearic, salicyclic, methanesulfonic, benzenesulfonic, sorbic, picric, benzoic, and cinnamic acids.

The compounds of the invention can also exist as solvates and hydrates. Thus, these compounds may crystallize with, for example, waters of hydration, or one, a number of, or any fraction of molecules of the mother liquor solvent. The solvates and hydrates of such compounds are included within the scope of this invention.

Often, ranges are expressed herein as from "about" one particular value and/or to "about" another particular value. When such a range is expressed, an embodiment includes the range from the one particular value and/or to the other particular value. Similarly, when values are expressed as approximations, by use of the word "about," it will be understood that the particular value forms another embodiment. It will be further understood that the endpoints of each of the ranges are significant both in relation to and independently of the other endpoint. As used herein the term "about" refers to ±10%.

"Optional" or "optionally" means that the subsequently described event or circumstance may or may not occur, and that the description includes instances where said event or circumstance occurs and instances where it does not. For example, the phrase "optionally comprising an agent" means that the agent may or may not exist.

It must be noted that, as used in the specification and the appended claims, the singular forms "a," "an" and "the" include plural referents unless the context clearly dictates otherwise. Thus, unless otherwise required by context, singular terms shall include the plural and plural terms shall include the singular.

The term "subject" as used herein denotes any animal, preferably a mammal, and more preferably a human. The examples of subjects include humans, non-human primates, rodents, guinea pigs, rabbits, sheep, pigs, goats, cows, horses, dogs and cats.

The term "effective amount" of an active ingredient as provided herein means a sufficient amount of the ingredient to provide the desired regulation of a desired function, such as gene expression, protein function, or the induction of a particular type of response. As will be pointed out below, the exact amount required will vary from subject to subject, depending on the disease state, physical conditions, age, sex, species and weight of the subject, the specific identity and formulation of the composition, etc. Dosage regimens may be adjusted to induce the optimum therapeutic response. For example, several divided doses may be administered daily or the dose may be proportionally reduced as indicated by the exigencies of the therapeutic situation. Thus, it is not possible to specify an exact "effective amount." However, an appropriate effective amount can be determined by one of ordinary skill in the art using only routine experimentation.

The term "treating" or "treatment" as used herein denotes reversing, alleviating, inhibiting the progress of, or improving the disorder or condition to which such term applies, or one or more symptoms of such disorder or condition.

The term "carrier" or "excipient" as used herein refers to any substance, not itself a therapeutic agent, used as a carrier and/or diluent and/or adjuvant, or vehicle for delivery of a therapeutic agent to a subject or added to a formulation to improve its handling or storage properties or to permit or facilitate formation of a dose unit of the composition into a discrete article such as a capsule or tablet suitable for oral administration. Suitable carriers or excipients are well known to persons of ordinary skill in the art of manufacturing pharmaceutical formulations or food products. Carriers or excipients can include, by way of illustration and not limitation, buffers, diluents, disintegrants, binding agents, adhesives, wetting agents, polymers, lubricants, glidants, substances added to mask or counteract a disagreeable taste or odor, flavors, dyes, fragrances, and substances added to improve appearance of the composition. Acceptable carriers or excipients include citrate buffer, phosphate buffer, acetate buffer, bicarbonate buffer, stearic acid, magnesium stearate, magnesium oxide, sodium and calcium salts of phosphoric and sulfuric acids, magnesium carbonate, talc, gelatin, acacia gum, sodium alginate, pectin, dextrin, mannitol, sorbitol, lactose, sucrose, starches, gelatin, cellulosic materials (such as cellulose esters of alkanoic acids and cellulose alkyl esters), low melting wax cocoa butter, amino acids, urea, alcohols, ascorbic acid, phospholipids, proteins (for example, serum albumin), ethylenediamine tetraacetic acid (EDTA), dimethyl sulfoxide (DMSO), sodium chloride or other salts, liposomes, mannitol, sorbitol, glycerol or powder, polymers (such as polyvinyl-pyrrolidone, polyvinyl alcohol, and polyethylene glycols), and other pharmaceutically acceptable materials. The carrier should not destroy the pharmacological activity of the therapeutic agent and should be non-toxic when administered in doses sufficient to deliver a therapeutic amount of the agent.

The invention provides a spiroenone of formula (I):

formula (I)

or a pharmaceutically acceptable derivative thereof, wherein $R_1$ to $R_4$ is dependently H or an alkyl group having 1 to 6 carbon atoms.

In some preferred embodiments of the spiroenone of formula (I), wherein $R_1$ to $R_4$ is dependently a methyl group.

In a more preferred embodiment of the invention, the spiroenone is formula (II).

formula (II)

The spiroenone of the invention is preferably further converted into a pharmaceutically acceptable derivative, such as a pharmaceutically acceptable salt, solvate or prodrug, by any known methods.

The present invention also provides a composition comprising the lacram of formula (I) or a pharmaceutically acceptable derivative thereof. The composition of the invention is preferably a food composition or a pharmaceutical composition. The spiroenone of formula (I) of the present invention is preferably provided in the form of an alcohol extract of dehulled adlay seeds or a chemical compound.

The spiroenone of formula (I) or a pharmaceutically acceptable derivative thereof or the alcohol extract of dehulled adlay seeds containing the spiroenone of formula (I) or a pharmaceutically acceptable derivative thereof can be added to a conventional food composition (i.e. the edible food or drink or precursors thereof) in the manufacturing process of the food composition. Almost all food compositions can be supplemented with the alcohol extract of dehulled adlay seeds of the invention. The food compositions that can be supplemented with the alcohol extract of dehulled adlay seeds of the invention include, but are not limited to, candies, baked goods, ice creams, dairy products, sweet and flavor snacks, snack bars, meal replacement products, fast foods, soups, pastas, noodles, canned foods, frozen foods, dried foods, refrigerated foods, oils and fats, baby foods, or soft foods painted on breads, or mixtures thereof.

The pharmaceutical composition of the invention is preferably administered topically or systemically by any method known in the art, including, but not limited to, intramuscular, intradermal, intravenous, subcutaneous, intraperitoneal, intranasal, oral, mucosal or external routes. The appropriate route, formulation and administration schedule can be determined by those skilled in the art. In the present invention, the pharmaceutical composition can be formulated in various ways, according to the corresponding route of administration, such as a liquid solution, a suspension, an emulsion, a syrup, a tablet, a pill, a capsule, a sustained release formulation, a powder, a granule, an ampoule, an injection, an infusion, a kit, an ointment, a lotion, a liniment, a cream or a combination thereof. If necessary, it may be sterilized or mixed with any pharmaceutically acceptable carrier or excipient, many of which are known to one of ordinary skill in the art; see paragraph [0028] for example.

Figure 1:
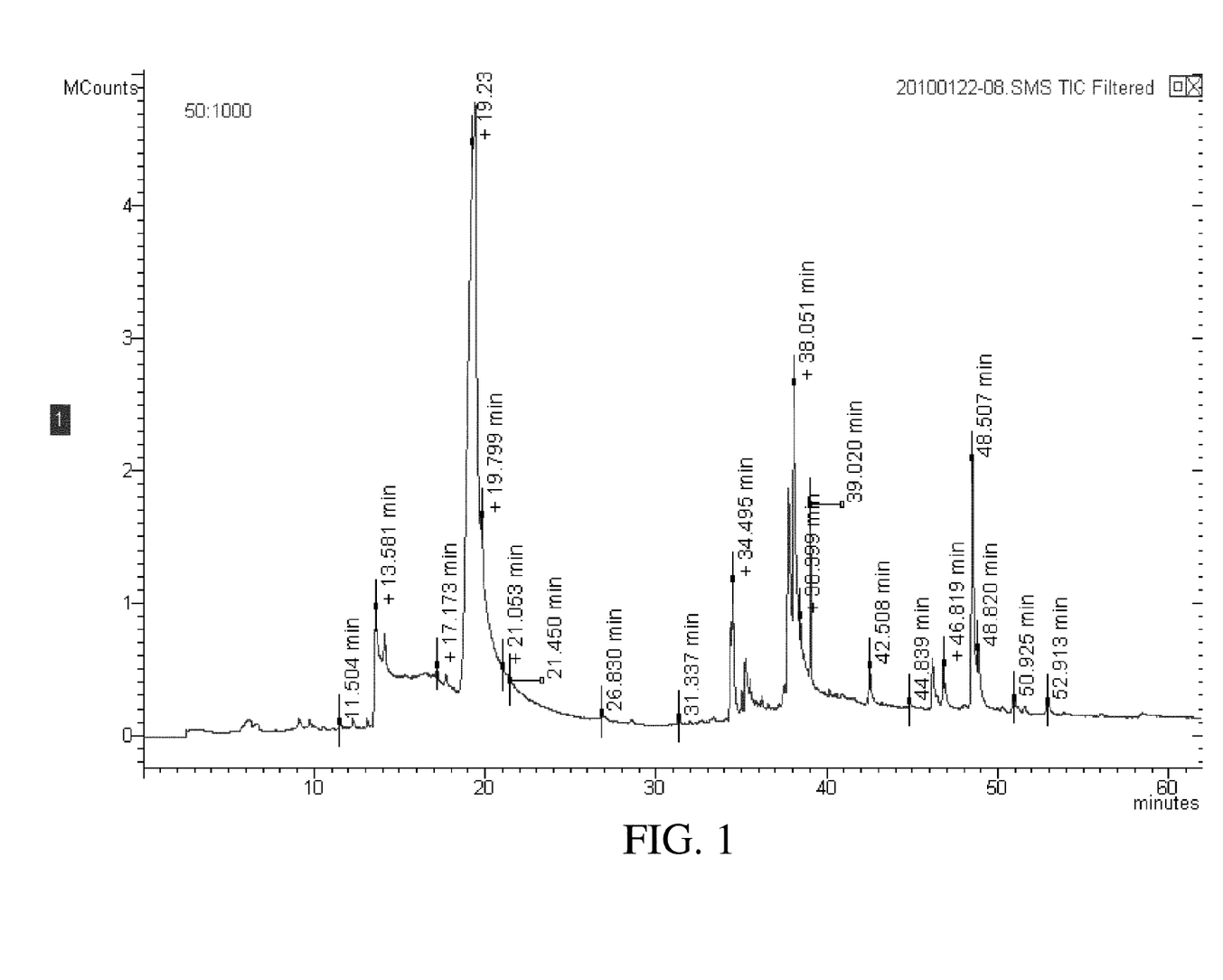
FIG. 1 illustrates the GC-MS spectrogram of the alcohol extract of dehulled adlay seeds according to the invention.

In one preferred embodiment of the invention, the alcohol extract of dehulled adlay seeds is subjected to a Gas Chromatography-Mass Spectrophotometry (GC-MS) assay. The gas chromatography is conducted with Varian® 450-GC; and the mass spectrophotometry is conducted with Varian® 240-MS; the column is Varian® VF-5 ms 30 m×0.25 mm (I.D. 0.25 μm). The temperature program is 150° C. for 5 min; heating to 200° C. at a rate of 10° C./min for 20 min; and heating to 280° C. at a rate of 10° C./min for 25 min. As shown in FIG. 1, the spectrogram obtained comprises peaks at retention time of about 13.581 min, about 19.237 min, 19.334 min, about 19.435 min, about 19.799 min, about 37.75 min, about 38.051 min, about 48.504 min and about 48.819 min (Table 1).

TABLE 1

| Retention time (min) | Area (%) |
|---|---|
| 13.581 | 2.65 |
| 19.237 | 35.17 |
| 19.334 | 6.68 |
| 19.435 | 20.60 |

TABLE 1-continued

| Retention time (min) | Area (%) |
|---|---|
| 19.799 | 4.11 |
| 37.75 | 7.70 |
| 38.051 | 11.94 |
| 48.504 | 8.56 |
| 48.819 | 2.60 |

Figure 2:
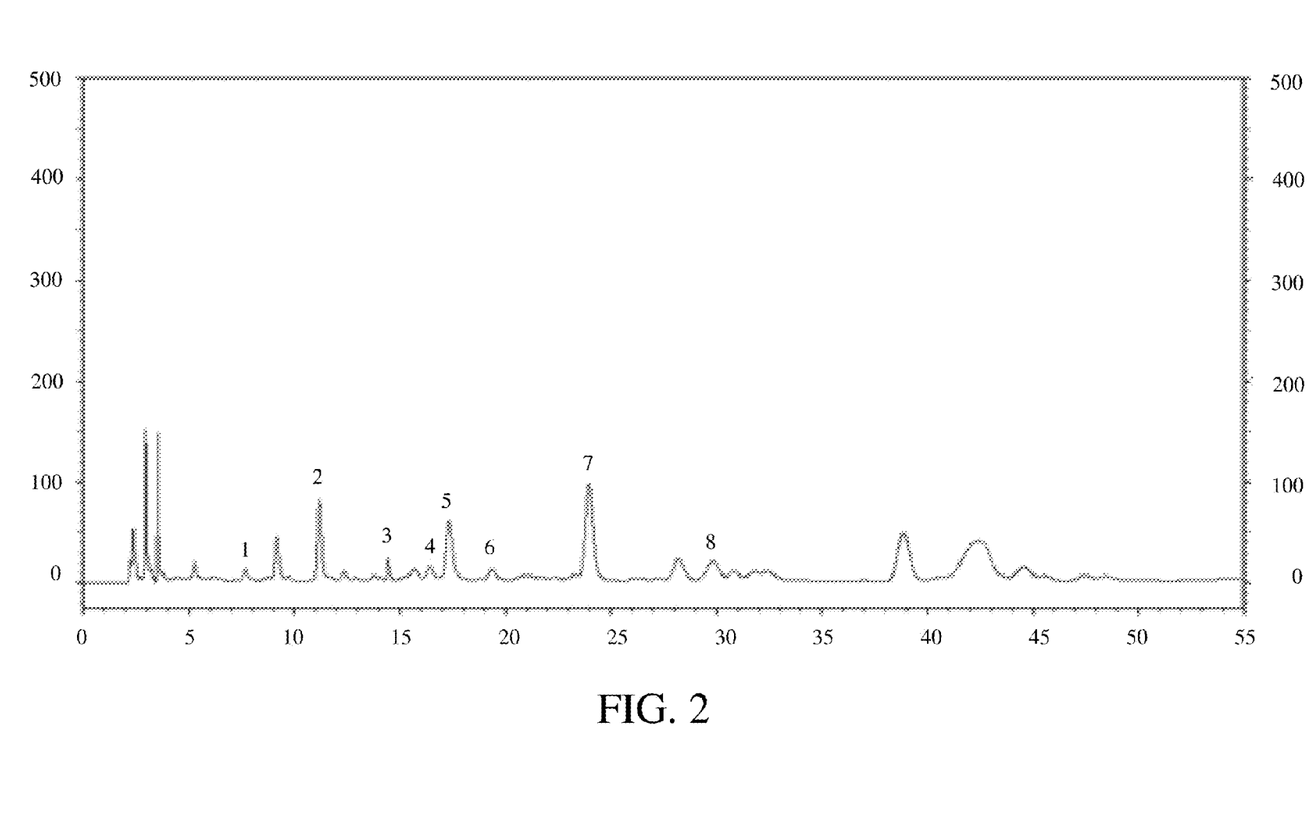
FIG. 2 illustrates the HPLC spectrogram of the alcohol extract of dehulled adlay seeds according to the invention.

In one preferred embodiment of the invention, the alcohol extract of dehulled adlay seeds is subjected to a high performance liquid chromatography assay. The column is Reverse phase C18 column (250×4.6 mm i.d.; YMC Co., INC). The column temperature is 40° C. The chromatograms are extracted at 280 nm and 320 nm. The mobile phase uses Solution A: 5% acetic acid in water; Solution B: 0.5% acetic acid in water/100% acetonitrile (1:1, v/v). The gradient elution program is shown in Table 2. As shown in FIG. 2, the spectrogram obtained comprises peaks at retention time of about 7.5 min, about 12.1 min, 14.4 min, about 16.1 min, about 16.8 min, about 18.9 min, about 23.3 min, and about 29.1 min.

TABLE 2

| Time (min) | Flow rate (mL/min) | Mobile phase A (%) | Mobile phase B (%) |
|---|---|---|---|
| 0 | 1.0 | 90 | 10 |
| 10 | 1.0 | 85 | 15 |
| 20 | 1.0 | 84 | 16 |
| 35 | 1.0 | 83 | 17 |
| 50 | 1.0 | 79 | 21 |
| 55 | 1.0 | 79 | 21 |

The dehulled adlay seeds comprise bran and endosperm, therefore, the alcohol extract of dehulled adlay seeds according to the invention preferably comprises an alcohol extract of adlay bran and an alcohol extract of adlay endosperm. The manner for obtaining the bran and endosperm from the dehulled adlay seeds is well-known to artisans skilled in this field.

In one preferred embodiment of the invention, the alcohol extract of dehulled adlay seeds is an ethanol extract of dehulled adlay seeds.

In one preferred embodiment of the invention, the spiroenone of formula (I) of the present invention is preferably provided in the form of an ethyl acetate sub-fraction of the alcohol extract of dehulled adlay seeds.

In one preferred embodiment of the invention, the spiroenone is prepared according to a process comprising the steps of:
  (a) providing adlay bran from dehulled adlay seeds;
  (b) extracting the adlay bran in step (a) with an ethanol solution to obtain an ethanol extract;
  (c) sequential partitioning the ethanol extract in step (b) with hexane and ethyl acetate to obtain an ethyl acetate fraction;
  (d) subfractioning the ethyl acetate fraction in step (c) with column chromatography with successive elution by an ethyl acetate/hexane gradient and methanol solvent to obtain an ethyl acetate/hexane subfraction; and
  (e) isolating the spiroenone from the subfraction in step (d) by high-performance liquid chromatography.

The term "dehulled adlay seeds" as used herein refers to seeds of adlay without hulls, testas, coverings, shells, or pods. The manner of removing the hulls, coverings, shells or pods from the adlay seeds is well-known to artisans skilled in this field. If needed, the bran and/or endosperm is further isolated from the dehulled adlay seeds.

The adlay seeds referred to in this invention are not particularly limited. Preferably, the adlay belongs to Gramineae family, Panicoideae sub-family, and *Coix* species, or Poales order, Poaceae family, and *Coix* species. More preferably, the adlay is *Coix lachryma-jobi, Coix lachryma-jobi* L., *Coix lachryma-jobi* L. var. *ma-yuen* Stapf, *Coix agrestis Lour., Coix arundinacea Lam., Coix exaltata Jacq., Coix lacryma* L.

According to the process of the invention, prior to step (b), the dehulled adlay seeds are preferably dried.

In one preferred embodiment of the invention, step (b) further comprises blending the small pieces into powder. The manner of cutting and/or blending is well-known to artisans skilled in this field.

The term "an alcohol extract of dehulled adlay seeds" as used herein refers to an extract of dehulled adlay seeds obtained by extracting the seeds with an alcohol solution. The manner of extracting the seeds with a solution is well-known to artisans skilled in this field. In one preferred embodiment of the invention, the dehulled adlay seeds are soaked in an alcohol solution for extraction.

The ratio (w/v) of the dehulled adlay seeds and the alcohol solution is not specifically restricted, and can be about 1:1 to about 1:10; preferably about 1:3 to about 1:8; and most preferably about 1:5.

In one preferred embodiment of the invention, the alcohol is selected from the group consisting of methanol, ethanol, n-propanol, isopropanol, n-butanol, iso-butanol, sec-butanol, tert-butanol, and ethanol acetate. More preferably, the alcohol is methanol or ethanol; most preferably, the alcohol is ethanol. The alcohol solution preferably about 90% to about 99.9% ethanol.

Preferably, the process further comprises (d) obtaining a liquid fraction from the extract, and a solid fraction is removed. The manner of removing the solid fraction to obtain the liquid fraction is well-known to artisans skilled in this field.

The invention also provides a method for treating inflammation in a subject, which comprises administering to said subject an effective amount of the spiroenone as mentioned above and a pharmaceutically acceptable carrier or excipient.

The following examples are given for the purpose of illustration only and are not intended to limit the scope of the present invention.

Example

Materials and Methods

General Experimental Procedures. The MCF-7, T-47D, MDAMB-231, and H184B5F5/M10 cell lines were obtained from the Bioresource Collection and Research Center (Hsinchu, Taiwan). Fetal bovine serum (FBS), minimum essential medium (MEM), MEM-R, Leibovitz's L-15, and RPMI-1640 medium were purchased from GIBCO (Grand Island, N.Y.). Penicillin, streptomycin, glutamine, 3-(4,5-dimethyl-2-thiazolyl)-2,5-diphenyl-2H-tetrazolium bromide (MTT), and other chemicals were obtained from Sigma (St. Louis, Mo.). Silica gel (230-400 mesh, Merck, Darmstadt, Germany), Sephadex LH-20 (Amersham Biosciences, Uppsala, Sweden), and a semi-preparative Si column (LiChrosorb Si-60, Merck) were used for column chromatography. Dimethyl sulfoxide (DMSO) and other solvents (analytical grade) were purchased from Merck. Infrared (IR) spectra were recorded on a Nicolet Avatar 320 FTIR spectrophotometer (Thermo Electron, Akron, Ohio). Optical rotation was measured on a Jasco P-2000 polarimeter (Hachioji, Tokyo, Japan). Nuclear magnetic resonance (NMR) spectra were run in $CDCl_3$ or $CD_3OD$ on a Varian unity INOVA-500 or VNMRS 600 (Varian, Palo Alto, Calif.). Electrospray ionization (ESI)-mass spectra (MS) were recorded on a Finnigan MAT LCQ ion-trap mass spectrometer system (Thermoquest, San Jose, Calif.).

Extraction and Fractionation. Adlay seeds (Taichung Shuenyu No. 4) were purchased from Taichung, Taiwan, 2009. The dried seeds were divided into the hull, testa, bran, and endosperm by a grinder and gently blown with an electric fan. A total of 25 kg of AB powder was soaked in 125 L of 95% ethanol at room temperature for 48 h. The ethanolic extract was combined and concentrated under reduced pressure at 50° C. to give 2834 g of ABE (10.9% of AB). The ABE was suspended in $H_2O$, which was followed by sequential partitioning with n-hexane (Hex), ethyl acetate (EA), and 1-butanol (BuOH) to give Hex-, EA-, BuOH—(ABE-BuOH, 42 g), and water-soluble fractions (ABE-$H_2O$, 258 g) according to the reported literature (Lee, M. Y.; Tsai, S. H.; Kuo, Y. H.; Chiang, W. Anti-tumor and anti-inflammatory activity of the methanol extracts from adlay bran. *Food Sci. Biotechnol.* 2008, 17, 1265-1271). The ABE-Hex was then repartitioned with 70% ethanol/$H_2O$ to extract the higher polar components in this fraction, and the 70% ethanol/$H_2O$ fraction was combined with ABE-EA to give 1720 g of ABE-Hex (60.7% of ABE) and 204 g of ABE-EA (7.2% of ABE). The four fractions were screened for antiproliferative potency on MCF-7 and MDA-MB-231 cells.

Cell Lines and Culture. MCF-7, T-47D, and H184B5F5/M10 cells were cultured with 5% $CO_2$ atmosphere at 37° C.; MDA-MB-231 cells were cultured without $CO_2$ at 37° C. The MCF-7 cells were cultured in MEM containing 10% heat-inactivated FBS, 100 units/mL penicillin, 100 μg/mL streptomycin, and 1 mM sodium pyruvate. The T-47D cells were maintained in RPMI-1640 medium containing 10% heat inactivated FBS, 100 units/mL penicillin, and 100 μg/mL streptomycin. The H184B5F5/M10 cells were grown in MEM-R medium containing 10% heat-inactivated FBS, 100 units/mL penicillin, and 100 μg/mL streptomycin as previously described (Ho, C. Y.; Kim, C, F.; Leung, K. N.; Fung, K. P.; Tse, T. F.; Chan, H.; Lau, C. B. Differential anti-tumor activity of *Coriolus versicolor* (Yunzhi) extract through p53- and/or Bcl-2-dependent apoptotic pathway in human breast cancer cells. *Cancer Biol. Ther.* 2005, 4, e11-e17). The MDA-MB-231 cells were cultured in Leibovitz's L-15 containing 10% heat-inactivated FBS, 100 units/mL penicillin, and 100 μg/mL streptomycin (Woo, J. H.; Li, D.; Wilsbach, K.; Orita, H.; Coulter, J.; Tully, E.; Kwin, T. K.; Xu, S.; Gabrielson, E. *Coix* seed extract, a commonly used treatment for cancer in China, inhibits NFκB and protein kinase C signaling. *Cancer Biol. Ther.* 2007, 6, 2005-2010).

Assay for Antiproliferation. To determine the antiproliferative effect, MCF-7, T-47D, MDA-MB-231, or H184B5F5/M10 cells were assessed using the MTT assay as previously reported (Ho, C. Y.; Kim, C. F.; Leung, K. N.; Fung, K. P.; Tse, T. F.; Chan, H.; Lau, C. B. Differential anti-tumor activity of *Coriolus versicolor* (Yunzhi) extract through p53- and/or Bcl-2-dependent apoptotic pathway in human breast cancer cells. *Cancer Biol. Ther.* 2005, 4, e11-e17). All of the test samples mentioned above were dissolved in DMSO, and the final concentration of DMSO was <0.1%. In addition, 0.1% DMSO was used as a blank vehicle. MCF-7, T-47D, MDA-MB-231, or H184B5F5/M10 cells were cultured in 96-well plates at a density of $1\times10^5$ cells/well and allowed to grow for 18-24 h. After this, the medium was replaced by FBS-free MEM, RPMI-1640, L-15, or MEM-R; then the various test samples in DMSO were added, and the cells were incubated for an additional 24 h. Next, MTT solution in FBS-free MEM, RPMI-1640, L-15, or MEMR, which had been filtered through a 0.45 mm membrane, was added to each well (final concentration of 0.5 mg/mL) The plates were incubated under a 5% $CO_2$ atmosphere at 37° C. for 20 min. The medium with unreacted dye was removed. DMSO was added into each well to dissolve the MTT formazan crystals, and the samples were incubated at room temperature for 5-10 min. The absorbance at 570 nm was measured, and the viability of cells was calculated using the following equation: relative cell number (%)=(average absorbance of treated wells)×100/(average absorbance of blank vehicle wells).

Isolation and Purification Process. The total ABE-EA fraction was subjected to silica gel column chromatography and elution with a Hex/EA/MeOH gradient solvent system to give five subfractions, namely, low polarity waste (20% EA/Hex eluate), ABE-EA-A (40% EA/Hex eluate), ABE-EA-B (70% EA/Hex eluate), ABE-EA-C (100% EA eluate), and ABE-EA-D (100% MeOH eluate). The ABE-EA-A and ABE-EA-B were combined (47.1 g, 24.5% of ABE-EA) and further chromatographyed over a Sephadex LH-20 column (MeOH) to give a spiroenone-containing fraction (LCF, 13.2 g) by the Dragendorff reagent (Hsia, S. M.; Tseng, Y. W.; Wang, S. W.; Kuo, Y. H.; Huang, D. W.; Wang, P. S.; Chiang, W. Effect of adlay (*Coix lachryma-jobi* L. var. *ma-yuen* Stapf.) hull extracts on testosterone release from rat Leydig cells. *Phytother. Res.* 2009, 23, 687-695). The LCF subfraction was further purified over a Saphadex LH-20 column using an EA/$CH_2Cl_2$ gradient to yield the following subfractions: 5% EA/$CH_2Cl_2$ (LCF-A, 0.91 g, 6.82% of LCF), 10% EA/$CH_2Cl_2$ (LCF-B, 2.14 g, 16.22% of LCF), 20% EA/$CH_2Cl_2$ (LCF-C, 2.21 g, 16.65% of LCF), 40% EA/$CH_2Cl_2$ (LCF-D, 3.59 g, 33.28% of LCF), 60% EA/$CH_2Cl_2$ (LCF-E, 0.92 g, 6.96% of LCF), 80% EA/$CH_2Cl_2$ (LCF-F, 0.82 g, 6.22% of LCF), EA (LCF-G, 0.54 g, 5.11% of LCF), and methanol (LCF-H, 1.64 g, 12.42% of LCF). The 40-60% EA/$CH_2Cl_2$ subfractions from the LCF were regarded as the spiroenone-enriched fraction (LEF) as previously described (Lee, M. Y.; Lin, H. Y.; Cheng, F.; Chiang, W. C.; Kuo, Y. H. Isolation and characterization of new spiroenone compounds that inhibit lung and colon cancer cells from adlay (*Coix lachryma-jobi* L. var. *mayuen* Stapf) bran. *Food Chem. Toxicol.* 2008, 46, 1933-1999) and were further purified by Sephadex LH-20 column chromatography (MeOH) and preparative high-performance liquid chromatography (HPLC) on a LiChrosorb Si-60 column (5 μm, Agilent, Santa Clara, Calif.) using EA/acetone/Hex=1:2:5, 1:2:4, or 1:2:3 as the mobile phase. The coixspiroenone (3, formula (II)) (2.7 mg) was isolated.

Figure 3:
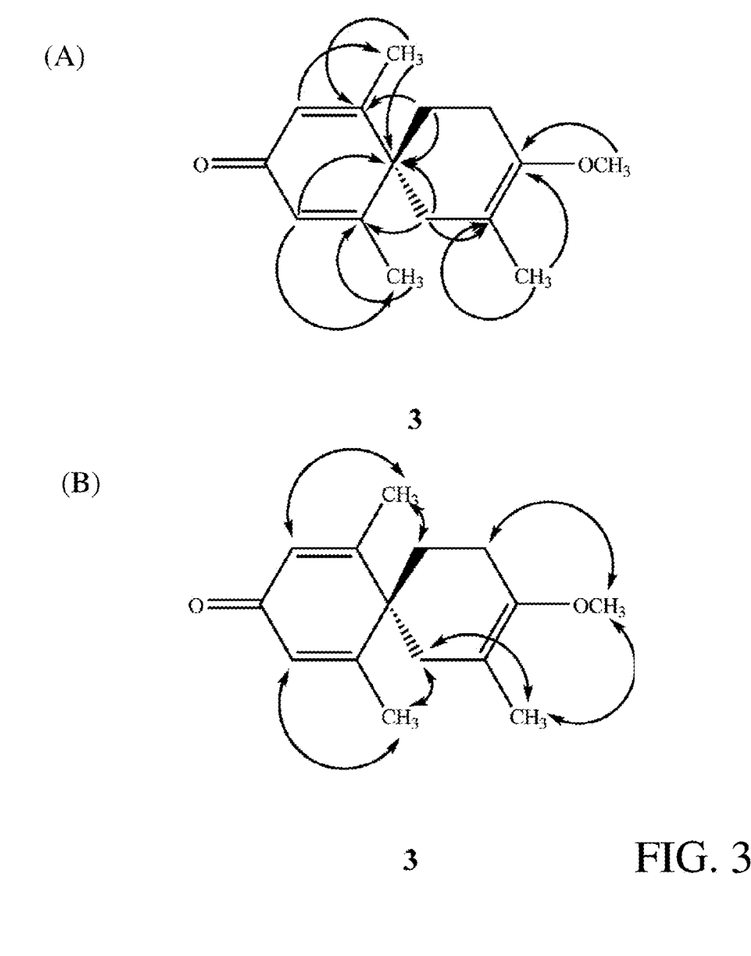
FIG. 3 illustrates key (A) HMBCs (f) and (B) NOESY correlations (T) of compound 3.

Coixspiroenone (3). Colorless oil. $[\alpha]^{25}_D \pm 0$ (c 0.20, MeOH). UV (MeOH) $\lambda_{max}$, nm (log ε): 243 (4.20). ESI-MS m/z (%): 255 (100, [M+Na]$^+$). IR (KBr) $\lambda_{max}$ (cm$^{-1}$): 1711, 1659, 1624, 1196, 1105. The $^1$H and $^{13}$C NMR data are presented in Table 3, and the key HMBCs and NOESY correlations are shown in FIG. 3.

TABLE 3

| Compound No. | 1 | | 2 | | 3 | | 9 | |
|---|---|---|---|---|---|---|---|---|
| | $\delta_H$ | $\delta_C$ | $\delta_H$ | $\delta_C$ | $\delta_H$ | $\delta_C$ | $\delta_H$ | $\delta_C$ |
| 3 | | 53.4 s | | 53.7 s | | 158.0 s | | 74.8 s |
| 3a | | 128.9 s | | 127.6 s | | | | 131.7 s | s, singlet. Chemical shifts are in δ (ppm). The coupling constants (J) are given in parentheses (Hz).

LC-MS Analysis. HPLC analysis was performed using a Finnigan MAT pump (P4000, Finnigan) with an ultraviolet (UV) detector (UV2000, Finnigan). Gradient elution was performed with 0.01% formic acid aqueous solution (v/v, pH 3.30, A) and 50% acetonitrile (ACN) in methanol (v/v, B) at a constant rate of 0.3 mL/min through an ODS-3 (250×4.6 mm, 5 μm) reverse-phase column (Inertsil). Initial starting conditions were 20% B, at 0-10 min; increase from 20 to 40% B, at 10-30 min; increase from 40 to 60% B, at 30-40 min; increase from 60 to 75% B, at 40-50 min; increase from 75 to 78% B, at 50-60 min; increase from 78 to 80% B, at 60-70 min; increase from 80 to 100% B, at 70-80 min; and finally, decrease from 100 to 20% B, at original conditions. The absorbance was set at 280 nm. This system was coupled with a Finnigan MAT LCQ ion-trap mass spectrometer system (Finnigan MAT, San Jose, Calif.), which was operated in the ESI mode. An aliquot of the bioactive fraction (10 mg/mL, 20 μL) was directly introduced into the column through the autosampler (Finnigan MAT AS3000), with nitrogen being used as the nebulizing and drying gas. The operating parameters used were as follows: a gas temperature of 250° C., a spray needle voltage of 5 kV, a nebulizer pressure of 60 psi, and an auxiliary gas pressure of 30 psi. An ion trap containing helium damping gas was introduced following the protocols of manufacturer. The mass spectra were acquired in a m/z range of 100-1000 with 5 microscans and a maximum ion injection time of 200 min. The isolated compounds were confirmed with a retention time (tR) and were qualified by MS using either a negative or positive mode.

Statistical Analysis. The bar values are present as the mean (standard deviation (SD) from three independent experiments. The results among groups were analyzed by analysis of variance (ANOVA) and Student's t test. A p value of <0.05 is considered to show a significant difference.

Results and Discussion

Compound Isolation and Structural Elucidation. The LCF was further purified by Sephedax LH-20 column chromatography (CC) and semi-preparative HPLC over a Si-60 column to yield coixspirospiroenone (3).

Coixspiroenone (3) was isolated as a colorless oil. The molecular formula was suggested to be $C_{15}H_{20}O_2$ by ESI-MS. The combination of the molecular formula, $^{13}C$ NMR, and DEPT data confirmed compound 3 with six indices of hydrogen deficiency. The IR and UV spectra showed the presence of an R, β-unsaturated carbonyl ($v_{max}$, 1711 and 1659 cm$^{-1}$; $\lambda_{max}$, 243 nm, respectively). The $^1H$ and $^{13}C$ NMR (Table 3) showed three olefinic tertiary methyl groups [$\delta_H$ 1.97 (6H, s), $\delta_C$ 20.2 q; $\delta_H$ 1.87 (3H, s), $\delta_C$ 16.3 q], two dienone conjugated R-position olefinic protons [$\delta_H$ 6.05 (2H, s), $\delta_C$ 126.6 d], one methoxy group [$\delta_H$ 3.74 (3H, s), $\delta_C$ 51.4 q], and three methylene groups, including two mutual coupling methylene groups [$\delta_H$ 2.07 and 3.16 (2H each, t), $\delta_C$ 35.7 and 34.2 t, respectively] and one singlet methylene group [$\delta_H$ 2.66 (2H, s), $\delta_C$ 43.2 t], identified by COSY and HMQC spectra. The HMBC spectrum indicated correlations as follows: H-14 [$\delta_H$ 1.87 (3H, s)]/C-7 ($\delta_C$ 43.2 t), C-8 ($\delta_C$ 119.9 s)], and C-9 ($\delta_C$ 168.1 s); H-12 (H-13) [$\delta_H$ 1.97 (6H, s)]/C-2 (C-6) ($\delta_C$ 126.6 d), C-3 ($\delta_C$ 158.0 s), C-4 ($\delta_C$ 52.4 s), and C-5 ($\delta_C$ 163.3 s); methoxyl group [$\delta_H$ 3.74 (3H, s)]/C-9 ($\delta_C$ 168.1 s); H-7 ($\delta_H$ 2.66 s)/C-3, C-4, C-5, C-8, C-9, and C-11 ($\delta$C 35.7 t); and H-11 [$\delta_H$ 2.07 t (8.4)]/C-3, C-4, C-5, C-7, and C-10. These spectral data suggested that compound 3 had a spirodienone structure (formula (II)). For the anisotropic effect, the chemical shifts of C-3 and C-5 appeared at $\delta_C$ 158.0 s and $\delta_C$ 163.3, respectively. The structure of compound 3 was further confirmed by NOESY experiments, with NOE correlations between H-12 and H-2, H-7, and H-11; between H-14 and H-7; and between the methoxyl group and H-10, which was a novel compound, named coixspiroenone.

Compound That Suppresses Human Breast Cancer Cell Line Growth. In the example, the antiproliferation of AB on MCF-7 cells, which is an ER-positive metastatic adenocarcinoma cell line with wild-type p53 protein, on T-47D cells, which is an ER-positive ductal carcinoma but with a mutant p53 protein, and on MDAMB-231 cells, which is an ER-negative carcinoma, involved evaluation of the antiproliferative effects of various subfractions and isolated compounds from ABE. In these experiments, H184B5F5/M10 cells are normal human breast epithelia cells used as a control.

The isolated compounds were tested for antiproliferative effects by the MTT assay. The results indicated that MCF-7 cells were significantly inhibited by compound 3 at 50 μM, with the percentage of inhibition being 19.2% (FIG. 4).

Figure 4:
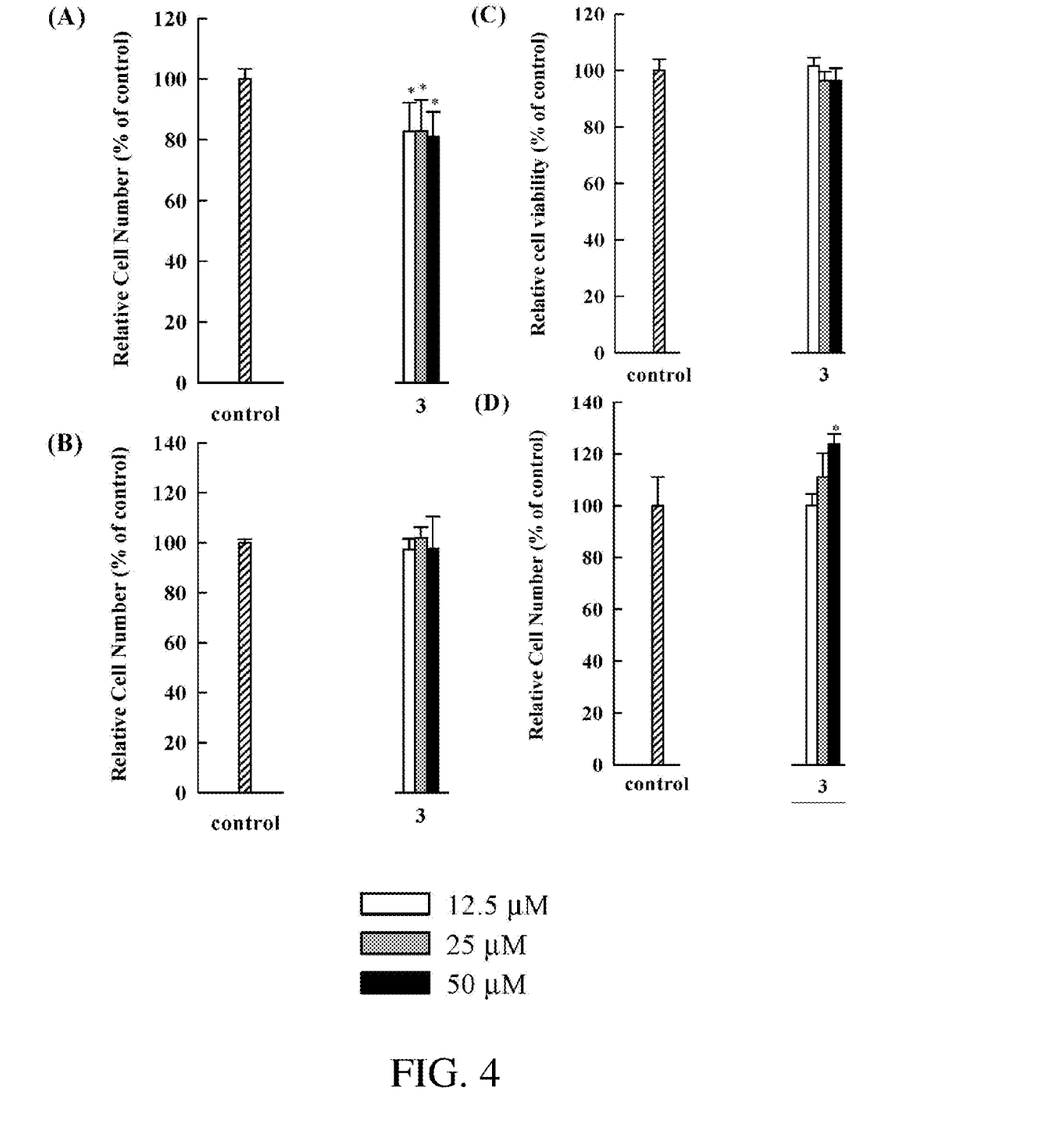
FIG. 4 illustrates the effects of isolated compounds on the cell proliferation of (A) MCF-7, (B) T-47D, (C) MDA-MB-231, and (D) H184B5F5/M10 cells. The cells were cultured with or without test samples for 24 h and examined using the MTT assay. The results are expressed as a percentage of living cells cultured in the presence of test samples relative to a parallel culture that did not receive any treatment. Each bar represents the mean±SD (n=3). (*) p<0.05 compared to the control group. (**) p<0.01 compared to the control group.

As shown in FIG. 4, the compounds isolated in the present study had more potency against MCF-7 cells than T-47D cells. P53 DNA repair might be one of the targeted pathways associated with this inhibition.

Figure 5:
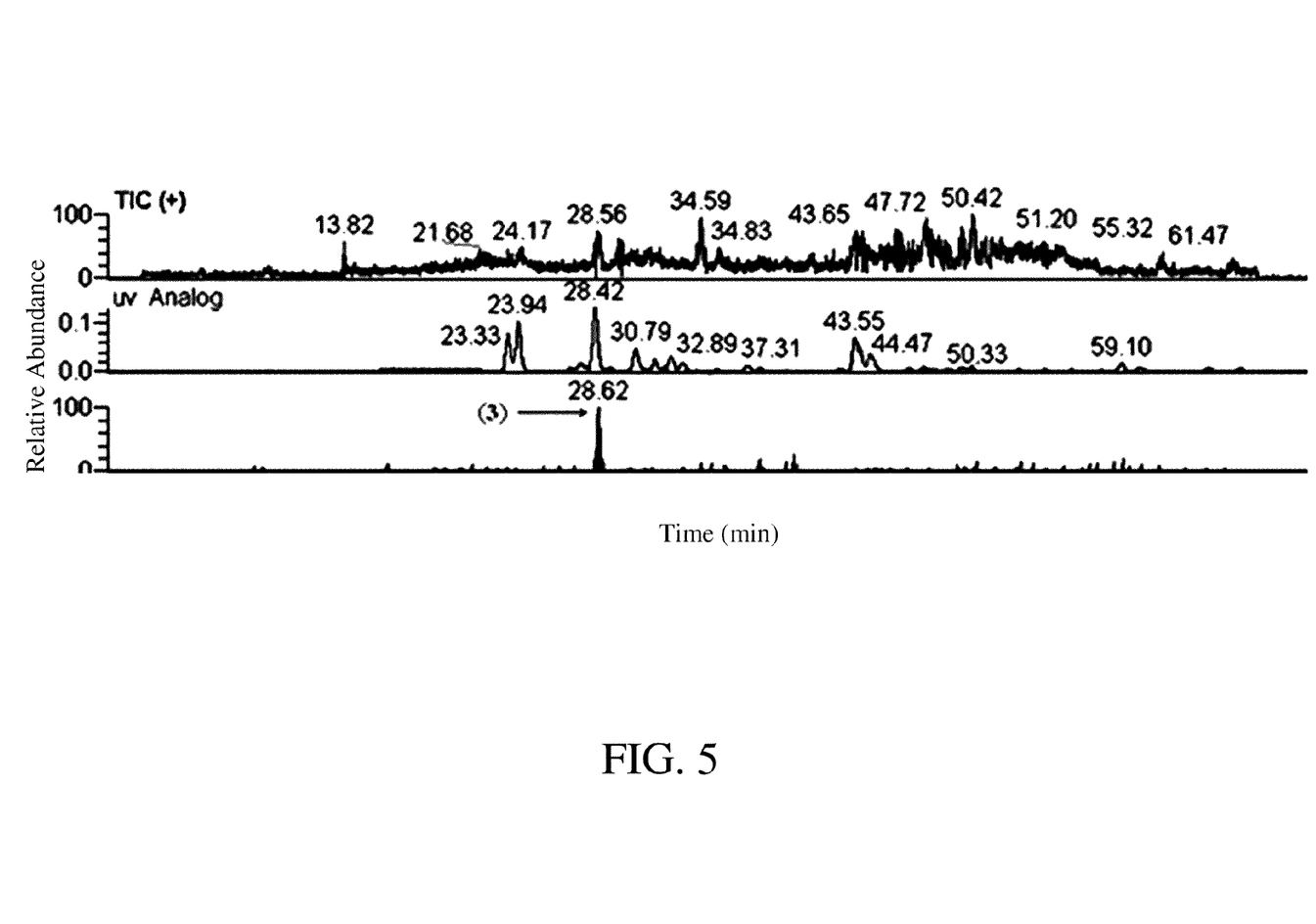
FIG. 5 illustrates LC-MS analytical spectrum of total positive-ion currents and UV chromatograms of ABE-EA-LEF.

LC-MS Analysis. LC-MS was applied to analyze ABE-EA. The total ion current (TIC) (lane 1) and UV chromatogram (lane 2) of LC-MS for the bioactive fraction are shown in FIG. 5. Peaks were identified for coixspiroenone (3) (tR, 28.62 min; [M+Na]$^+$ m/z, 255) in a positive-ion mode. From the above results, it is clear that the spiroenone (compound 3) needs the positive-ion mode. Overall, LC-MS analysis can be used as an analytical platform for the compound.

While embodiments of the present invention have been illustrated and described, various modifications and improvements can be made by persons skilled in the art. It is intended that the present invention is not limited to the particular forms as illustrated, and that all the modifications not departing from the spirit and scope of the present invention are within the scope as defined in the following claims.

What is claimed is:

1. A spiroenone of formula (I):

formula (I)

or a pharmaceutically acceptable derivative thereof,
wherein $R_1$ to $R_4$ is dependently H or an alkyl group having 1 to 6 carbon atoms.

2. The spiroenone according to claim 1, wherein $R_1$ to $R_4$ is dependently a methyl group.

3. The spiroenone according to claim 1, which is formula (II), formula (II)

4. The spiroenone according to claim 1, which is provided in the form of an alcohol extract of dehulled adlay seeds.

5. The spiroenone according to claim 4, wherein the spiroenone is provided in the form of an ethyl acetate subfraction of the alcohol extract of dehulled adlay seeds.

6. The spiroenone according to claim 4, wherein the adlay is *Coix lachryma-jobi* L. var. *ma-yuen* Stapf.

7. The spiroenone according to claim 4, wherein the alcohol is selected from the group consisting of methanol, ethanol, n-propanol, isopropanol, n-butanol, iso-butanol, sec-butanol, tert-butanol, and ethanol acetate.

8. A composition comprising the spiroenone according to claim 1 and optionally a pharmaceutically acceptable carrier or excipient.

9. The composition according to claim 8, wherein $R_1$ to $R_4$ is dependently a methyl group.

10. The composition according to claim 8, which is formula (II), formula (II)

11. The composition according to claim 8, wherein the spiroenone is provided in the form of an alcohol extract of dehulled adlay seeds.

12. The composition according to claim 11, wherein the spiroenone is provided in the form of an ethyl acetate subfraction of the alcohol extract of dehulled adlay seeds.

13. The composition according to claim 11, wherein the adlay is *Coix lachryma-jobi* L. var. *ma-yuen* Stapf.

14. The composition according to claim 11, wherein the alcohol is selected from the group consisting of methanol, ethanol, n-propanol, isopropanol, n-butanol, iso-butanol, sec-butanol, tert-butanol, and ethanol acetate.

15. A process for the preparation of the spiroenone according to claim 1, which process comprises the steps of:
(a) providing adlay bran from dehulled adlay seeds;
(b) extracting the adlay bran in step (a) with an alcohol solution to obtain an alcohol extract;
(c) sequential partitioning the ethanol extract in step (b) with hexane and ethyl acetate to obtain an ethyl acetate fraction;
(d) subfractioning the ethyl acetate fraction in step (c) with column chromatography with successive elution by an ethyl acetate/hexane gradient ant methanol solvent to obtain an ethyl acetate/hexane subfration; and
(e) isolating the spiroenone from the subfraction in step (d) by high-performance liquid chromatography.

16. The process according to claim 15, wherein the adlay is *Coix lachryma-jobi* L. var. *ma-yuen* Stapf.

17. The process according to claim 15, wherein the alcohol is selected from the group consisting of methanol, ethanol, n-propanol, isopropanol, n-butanol, iso-butanol, sec-butanol, tert-butanol, and ethanol acetate.

18. A method for treating breast cancer in a subject, which comprises administering to said subject an effective amount of the spiroenone according to claim 1 and a pharmaceutically acceptable carrier or excipient.

19. The method according to claim 18, wherein $R_1$ to $R_4$ is dependently a methyl group.

20. The method according to claim 18, which is formula (II), formula (II)

21. The method according to claim 18, wherein the spiroenone is provided in the form of an alcohol extract of dehulled adlay seeds.

22. The method according to claim 21, wherein the spiroenone is provided in the form of an ethyl acetate subfraction of the alcohol extract of dehulled adlay seeds.

23. The method according to claim 21, wherein the adlay is *Coix lachryma-jobi* L. var. *ma-yuen* Stapf.

24. The method according to claim 21, wherein the alcohol is selected from the group consisting of methanol, ethanol, n-propanol, isopropanol, n-butanol, iso-butanol, sec-butanol, tert-butanol, and ethanol acetate.

* * * * *